(12) United States Patent
Robinson et al.

(10) Patent No.: US 10,495,622 B2
(45) Date of Patent: Dec. 3, 2019

(54) BI-DIRECTIONAL OIL-FLOW ADAPTER FOR ATTACHING TO A VALVE-CONTROLLED PORT OF A TRANSFORMER

(71) Applicant: General Electric Technology GmbH, Baden (CH)

(72) Inventors: David Peter Robinson, Lisburn (GB); Alan McGregor, Lisburn (GB)

(73) Assignee: General Electric Technology GmbH, Baden (CH)

( * ) Notice: Subject to any disclaimer, the term of this patent is extended or adjusted under 35 U.S.C. 154(b) by 196 days.

(21) Appl. No.: 15/250,162

(22) Filed: Aug. 29, 2016

(65) Prior Publication Data

US 2018/0059087 A1 Mar. 1, 2018

(51) Int. Cl.
*G01N 33/28* (2006.01)
*G01N 1/02* (2006.01)
(Continued)

(52) U.S. Cl.
CPC .......... *G01N 33/2841* (2013.01); *F15D 1/02* (2013.01); *G01N 1/02* (2013.01); *H01F 27/12* (2013.01);
(Continued)

(58) Field of Classification Search
CPC ......... G01N 1/2035; G01N 2001/2064; G01N 33/2841; G01N 1/20; G01N 1/02;
(Continued)

(56) References Cited

U.S. PATENT DOCUMENTS 5,070,738 A * 12/1991 Morgan ................... G01N 1/14
73/863.83
5,271,263 A * 12/1993 Gibeault ................. G01M 3/20
73/19.12
(Continued)

FOREIGN PATENT DOCUMENTS

| CN | 105805403 A | 7/2016 |
|----|-------------|--------|
| EP | 2810041 A1 | 12/2014 |
| WO | 2013116799 A1 | 8/2013 |

OTHER PUBLICATIONS

Extended European Search Report and Opinion issued in connection with corresponding EP Application No. 17185593.5 dated Jan. 19, 2018.

*Primary Examiner* — Eric S. McCall
*Assistant Examiner* — Timothy P Graves
(74) *Attorney, Agent, or Firm* — Eversheds Sutherland (US) LLP (57) ABSTRACT

Certain embodiments of the disclosure relate to a bi-directional oil-flow adapter that is attachable to a valve-controlled port of a transformer housing in which oil is contained for cooling parts of the transformer such as a primary coil and a secondary coil. The bi-directional oil-flow adapter not only allows for an oil sample to be drawn out of the transformer housing via the valve-controlled port but also allows for the oil sample to be used (along with an additional volume of oil if so desired) for flushing the valve-controlled port in order to ensure that a subsequent oil sample is different than a current oil sample. The oil sample can be provided to a dissolved gas analyzer for detecting and analyzing one or more gases that may be present in the oil sample, the one more gases indicative of a level of contamination of the oil sample.

18 Claims, 5 Drawing Sheets

(51) Int. Cl.
  *F15D 1/02*   (2006.01)
  *H01F 27/12*  (2006.01)
  *H01F 27/40*  (2006.01)
  *H01F 27/14*  (2006.01)
  *F16K 3/00*   (2006.01)
  *G01N 1/20*   (2006.01)

(52) U.S. Cl.
  CPC ........... *H01F 27/14* (2013.01); *H01F 27/402* (2013.01); *F16K 3/00* (2013.01); *G01N 1/20* (2013.01)

(58) Field of Classification Search
  CPC ........ H01F 27/12; H01F 27/14; H01F 27/402; F15D 1/02; F16K 3/00
  See application file for complete search history.

(56) References Cited

U.S. PATENT DOCUMENTS

| | | | |
|---|---|---|---|
| 9,176,107 B2 | 11/2015 | Jeffrey et al. | |
| 2008/0127714 A1 | 6/2008 | Altmann | |
| 2012/0247185 A1* | 10/2012 | Herz | G01N 33/2841 73/31.04 |
| 2014/0053626 A1* | 2/2014 | Jeffrey | G01N 33/2841 73/19.1 |
| 2015/0287523 A1* | 10/2015 | Lyu | G01R 31/027 336/84 M |

\* cited by examiner

BI-DIRECTIONAL OIL-FLOW ADAPTER FOR ATTACHING TO A VALVE-CONTROLLED PORT OF A TRANSFORMER

TECHNICAL FIELD

This disclosure relates to a power transformer, and more particularly, to a bi-directional oil flow adapter for attaching to a valve-controlled port of a power transformer.

BACKGROUND

A power transformer typically includes a housing containing oil that is used to cool the coils of the power transformer. Over time, the oil deteriorates and becomes less efficient in operating as a cooling agent. Consequently, the oil contained inside the power transformer is periodically replaced with fresh oil. The oil replacement procedure is generally carried out by injecting fresh oil into a first valve-controlled port of the housing while draining out the old oil via a second valve-controlled port of the housing. Using such a draining procedure ensures that the fresh oil flushes out the old oil. However, this operation requires that various fixtures (piping, insulation, gaskets, tanks etc.) be provided on each of the two valve-controlled ports and, thus, reserved for performing oil replacement procedures.

BRIEF DESCRIPTION OF THE DISCLOSURE

Certain embodiments of the disclosure can provide a technical effect and/or solution to provide a bi-directional oil-flow adapter that can be attached to a valve-controlled port that is a part of a transformer housing in which oil is contained for purposes of cooling various parts of a transformer, such as a primary coil, a secondary coil, and a core. The bi-directional oil-flow adapter not only allows for an oil sample to be drawn out of the transformer housing via the valve-controlled port for various purposes, but also allows for the oil sample to combined with an additional volume of oil if so desired and used for flushing the valve-controlled port. The flushing can be carried out to ensure that a subsequent oil sample is different than a current oil sample. The one or more oil samples drawn out of the transformer can be provided to a dissolved gas analyzer (DGA) for purposes of detecting and analyzing one or more gases that may be present in the oil sample. The presence and/or concentration of these one or more gases can be used to detect a contaminant in the oil sample and/or to determine a level of contamination of the oil sample.

Accordingly, in one exemplary embodiment of the disclosure, a system can include a transformer, a bi-directional oil-flow adapter, and a dissolved gas analyzer. The transformer can include a valve-controlled port for use when accessing oil contained inside the transformer. The bi-directional oil-flow adapter can be attached to the valve-controlled port and can include an oil outlet port, a first conduit contained inside the bi-directional oil-flow adapter, an oil inlet port, and a second conduit contained inside the bi-directional oil-flow adapter. The oil outlet port can be configured to output an oil sample acquired from the transformer via the valve-controlled port and the bi-directional oil-flow adapter when the bi-directional oil-flow adapter can be attached to the valve-controlled port. The first conduit contained inside the bi-directional oil-flow adapter has a first cross-sectional area that is selected to provide a first oil flow velocity to the oil sample when flowing from the valve-controlled port and through the bi-directional oil-flow adapter to the oil outlet port. The oil inlet port can be configured to accept an inflow of a volume of oil into the bi-directional oil-flow adapter. The second conduit has a second cross-sectional area that is smaller than the first cross-sectional area, the second cross-sectional area selected to provide a second oil flow velocity to the volume of oil when flowing from the oil inlet port and through the bi-directional oil-flow adapter into the valve-controlled port. The second oil flow velocity is higher than the first oil flow velocity. The dissolved gas analyzer can be coupled to the oil outlet port of the bi-directional oil-flow adapter and is operable to analyze the oil sample for evaluating at least one gas content of the oil sample.

According to another exemplary embodiment of the disclosure, a bi-directional oil-flow adapter that is attachable to a valve-controlled port of a transformer can include an oil outlet port, a first conduit contained inside the bi-directional oil-flow adapter, an oil inlet port, and a second conduit contained inside the bi-directional oil-flow adapter. The oil outlet port can be configured to output an oil sample acquired from the transformer via the valve-controlled port and the bi-directional oil-flow adapter when the bi-directional oil-flow adapter is attached to the valve-controlled port. The first conduit has a first cross-sectional area that is selected to provide a first oil flow velocity to the oil sample when flowing from the valve-controlled port and through the bi-directional oil-flow adapter to the oil outlet port. The oil inlet port can be configured to accept an inflow of a volume of oil into the bi-directional oil-flow adapter. The second conduit has a second cross-sectional area that is smaller than the first cross-sectional area, the second cross-sectional area selected to provide a second oil flow velocity to the volume of oil when flowing from the oil inlet port and through the bi-directional oil-flow adapter into the valve-controlled port. The second oil flow velocity is higher than the first oil flow velocity.

According to yet another exemplary embodiment of the disclosure, a method can include providing a bi-directional oil-flow adapter connected to a valve-controlled port of a transformer; providing a dissolved gas analyzer that is coupled to an oil outlet port of the bi-directional oil-flow adapter; drawing oil from the valve-controlled port via a first conduit of the bi-directional oil-flow adapter, the first conduit having a first cross-sectional area that is selected to provide a first oil flow velocity; providing at least one oil sample to the dissolved gas analyzer, via the oil outlet port that is located at one end of the first conduit; analyzing, in the dissolved gas analyzer, the at least one oil sample for evaluating at least one gas content in the at least one oil sample; transferring the at least one oil sample from the dissolved gas analyzer to a purge tank containing a volume of oil; and pumping at least a portion of the volume of oil from the purge tank and into the valve-controlled port of the transformer via an oil inlet port located at one end of a second conduit of the bi-directional oil-flow adapter, the second conduit having a second cross-sectional area that is smaller than the first cross-sectional area of the first conduit, the second cross-sectional area providing a second oil flow velocity that is greater than the first oil flow velocity.

Other embodiments and aspects of the disclosure will become apparent from the following description taken in conjunction with the following drawings.

BRIEF DESCRIPTION OF THE DRAWINGS

Having thus described the disclosure in general terms, reference will now be made to the accompanying drawings, which are not necessarily drawn to scale, and wherein:

DETAILED DESCRIPTION

The disclosure will be described more fully hereinafter with reference to the accompanying drawings, in which exemplary embodiments of the disclosure are shown. This disclosure may, however, be embodied in many different forms and should not be construed as limited to the exemplary embodiments set forth herein; rather, these embodiments are provided so that this disclosure will satisfy applicable legal requirements. Like numbers refer to like elements throughout. It should be understood that certain words and terms are used herein solely for convenience and such words and terms should be interpreted as referring to various objects and actions that are generally understood in various forms and equivalencies by persons of ordinary skill in the art. It should be understood that the words "example" and "exemplary" as used herein are intended to be non-exclusionary and non-limiting in nature. More particularly, the word "exemplary" as used herein indicates one among several examples, and it should be understood that no undue emphasis or preference is being directed to the particular example being described.

Figure 1:
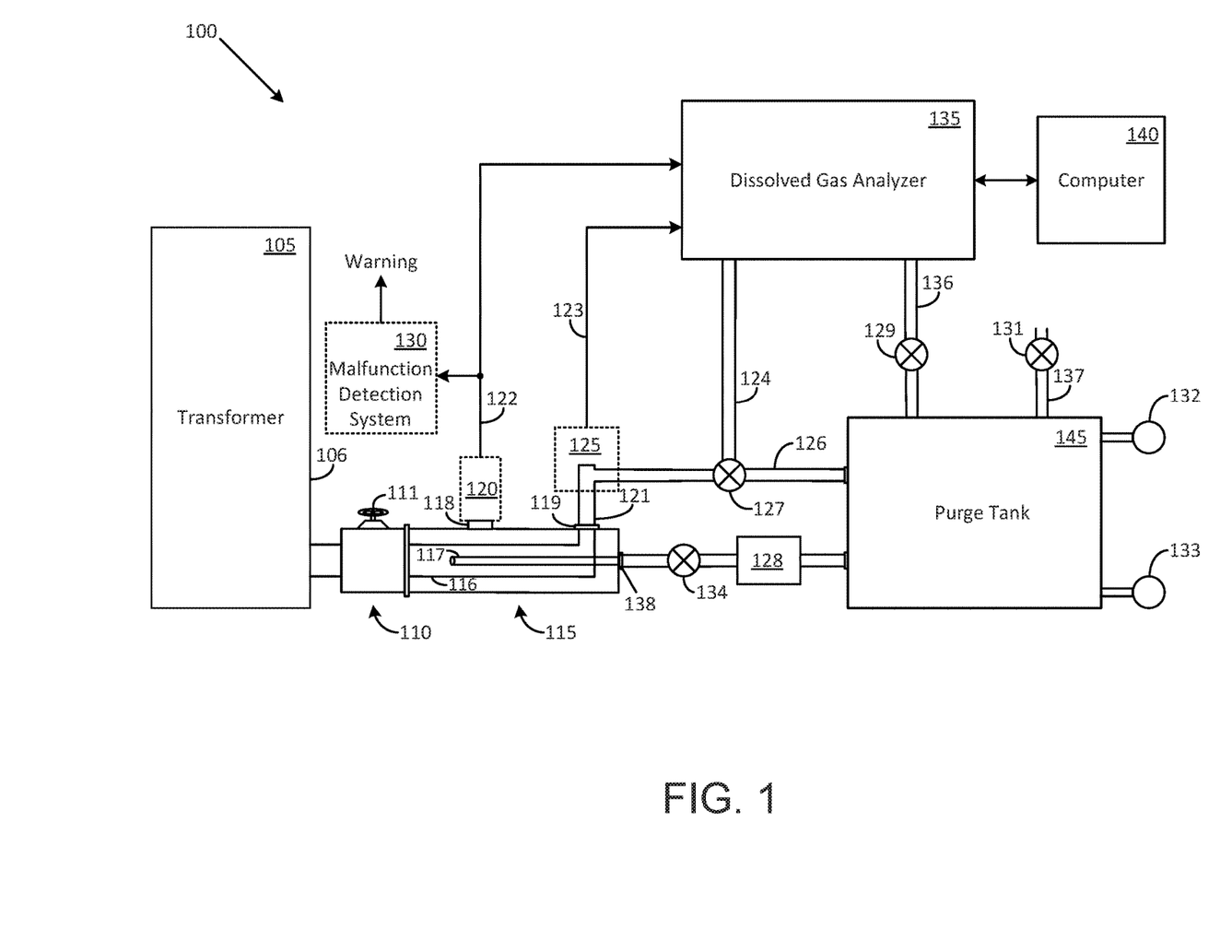
FIG. 1 shows an exemplary system that includes a transformer and a bi-directional oil-flow adapter attached to a valve-controlled port of a transformer housing in which some components of the transformer are housed, in accordance with an embodiment of the disclosure.

Attention is first drawn to FIG. 1, which shows an exemplary system 100 that can include a transformer 105 and a bi-directional oil-flow adapter 115 attached to a valve-controlled port 110 of a transformer housing 106 inside which various components of the transformer 105 are housed. The transformer housing 106 also contains oil that is used for cooling the various components of the transformer 105 contained inside, such as a primary coil and/or a secondary coil. The valve-controlled port 110 can be used in accordance with traditional practice for draining out old oil while replacing the old oil with fresh oil via another valve-controlled port (not shown). As can be understood, the valve-controlled port 110 can incorporate various traditional elements such as a gate valve, a butterfly valve, or a globe valve, each of which can be manually operated using a control wheel or lever, such as the control wheel 111 shown in FIG. 1.

In accordance with certain embodiments of the disclosure, the bi-directional oil-flow adapter 115 not only allows for an oil sample to be extracted out of the transformer housing 106 via the valve-controlled port 110 for various purposes, but also allows for the oil sample to be used in a flushing procedure for flushing the valve-controlled port. The flushing, which can be used to ensure that the contents in a subsequent oil sample are different than in a current oil sample, can be carried out by combining the extracted oil sample with an additional volume of oil stored in a purge tank 145, as will be described below in more detail.

The oil sample that is extracted from the transformer housing 106 via the valve-controlled port 110, can flow through a first conduit 116 inside the bi-directional oil-flow adapter 115 and out of an oil outlet port 119 of the bi-directional oil-flow adapter 115. The first conduit 116 can have a first cross-sectional area that can be specifically selected to provide a first oil flow velocity to the oil sample when flowing from the valve-controlled port 110 and through the bi-directional oil-flow adapter 115 to the oil outlet port 119.

In a procedure that will be described below in more detail, the oil sample can be transferred to a purge tank 145 after a dissolved gas analysis of the oil sample is carried out. The oil sample can be subsequently combined with a volume of oil that is optionally added to the purge tank 145, and forcefully reintroduced into the valve-controlled port 110 through an inlet port 138 for purposes of purging the valve-controlled port 110 of old and/or stagnant oil. The reintroduction procedure can be carried out by using a pump 128 to forcefully inject the oil sample combined, if so desired, with the volume of oil stored in the purge tank 145 back into the valve-controlled port 110 via a second conduit 117 contained inside the bi-directional oil-flow adapter 115. The second conduit 117 can have a second cross-sectional area that is relatively smaller than the first cross-sectional area of the first conduit 116 and can be specifically selected to provide a second oil flow velocity to the oil sample when flowing through the bi-directional oil-flow adapter 115 and into the valve-controlled port 110. The smaller cross-sectional area of the second conduit 117 can ensure, in certain instances, that the second oil flow velocity directed towards the valve-controlled port 110 is relatively higher than the first oil flow velocity out of the valve-controlled port 110.

An oil pipe section 121 can be coupled to the outlet port 119 for transporting the oil sample from the bi-directional oil-flow adapter 115 to a gas sensor assembly 125. The gas sensor assembly 125, which is an optional element and can be omitted in some implementations, can be configured to detect a rate of release of at least one gas contained in the oil sample and to generate one or more sensor signals that can be provided to a dissolved gas analyzer (DGA) 135 via a signal line 123. For example, the gas sensor assembly 125 can detect a rate of release of a gas contained in the oil sample and determine that the oil sample has a level of contamination that may warrant an analysis procedure in the DGA 135. The various gases processed by the gas sensor assembly 125 can include a family of gases, including a family of low-k gases such as hydrogen and/or carbon monoxide.

The oil pipe section 121 can be further coupled to a control valve 127 that can be activated to route the oil sample into the DGA 135 via an oil pipe section 124. In one example implementation, the oil sample can be drawn into the DGA 135 via the oil pipe section 124, by using a pump (not shown) that is located inside the DGA 135.

The DGA 135 can perform a gas analysis procedure to identify and/or measure the concentration of various gases in the oil sample so as to assess the quality of the oil sample. For example, the gas analysis procedure can be used to determine if the oil contained inside the transformer housing 106 warrants carrying out an oil replacement. Gas analysis procedures associated with the DGA 135 are known in the art and any number of such procedures can be performed by the DGA 135. In any instance, the results of the gas analysis procedure(s) performed by the DGA 135 can be provided to a computer 140 that is communicatively coupled to the DGA 135. The computer 140 can use the results of the gas analysis procedures for various purposes, such as to provide alarms, messages, and alerts to personnel associated with the transformer 105 (a technician, a manager, a data analyst etc.).

After executing one or more gas analysis procedures upon the oil sample, the DGA 135 can transfer the oil sample to the purge tank 145 via an oil pipe section 136 where oil flow can be controlled by using a control valve 129. It should be understood that the gas analysis procedure carried out by the DGA 135 can be repeated on several oil samples provided via the bi-directional oil-flow adapter 115. The several oil samples can be obtained over a period of time in a periodic or intermittent manner, as desired.

The purge tank 145 can be configured to not only store the oil sample provided by the DGA 135 via the oil pipe section 136, but to also store an additional volume of oil that can be directed into the purge tank 145 via an oil pipe section 126. Specifically, the control valve 127, which can be a directional valve to route oil into at least two different oil pipe sections, can not only be actuated to route the oil sample from the bi-directional oil-flow adapter 115 into the DGA 135, but can be also actuated to alternatively route an amount of oil (other than the oil sample) from the bi-directional oil-flow adapter 115 into the purge tank 145. The additional volume of oil can be combined with the oil sample provided by the DGA 135, if so desired, and used to forcefully purge the valve-controlled port 110 of old and/or stagnant oil. The pump 128 and a control valve 134 (optional) can be used for this purpose.

The purge tank 145 can include various elements such as a first level sensor 132 for sensing an oil level exceeding a high threshold level, and a second level sensor 133 for sensing an oil level dropping below a low threshold level. An air inlet assembly can also be provided in the form of an air inlet pipe 137 and a control valve 131 that can be actuated to allow air to enter the purge tank 145 via the air inlet pipe 137, if so desired. The air can be provided for example, when the oil stored in the purge tank 145 is being pumped out by the pump 128.

Attention is now drawn to a malfunction detection system 130 and a pressure sensor 120 shown in FIG. 1, each of which can be optionally included in some example implementations. The malfunction detection system 130 can be coupled to a signal line 122 that can carry one or more oil pressure signals or gas level indication signals from the pressure sensor 120 to the dissolved gas analyzer (DGA) 135. The pressure sensor 120 can be attached to the bi-directional oil-flow adapter 115 (at a pressure monitoring port 118) for monitoring an oil pressure and/or a gas pressure in the bi-directional oil-flow adapter 115. Changes in the oil pressure and/or the gas pressure can be indicative of various malfunctions, such as a malfunction in the valve-controlled port 110 and/or in the bi-directional oil-flow adapter 115. Upon detecting such a malfunction (based on processing the signal(s) carried on signal line 122), the malfunction detection system 130 can transmit various alarms, messages, and/or alerts to various personnel associated with the transformer 105 (such as a technician, a manager, and/or a data analyst). In some implementations, the malfunction detection system 130 can be communicatively coupled to the computer 140 for facilitating and/or processing of the various alarms, messages, and/or alerts by the computer 140.

Figure 2:
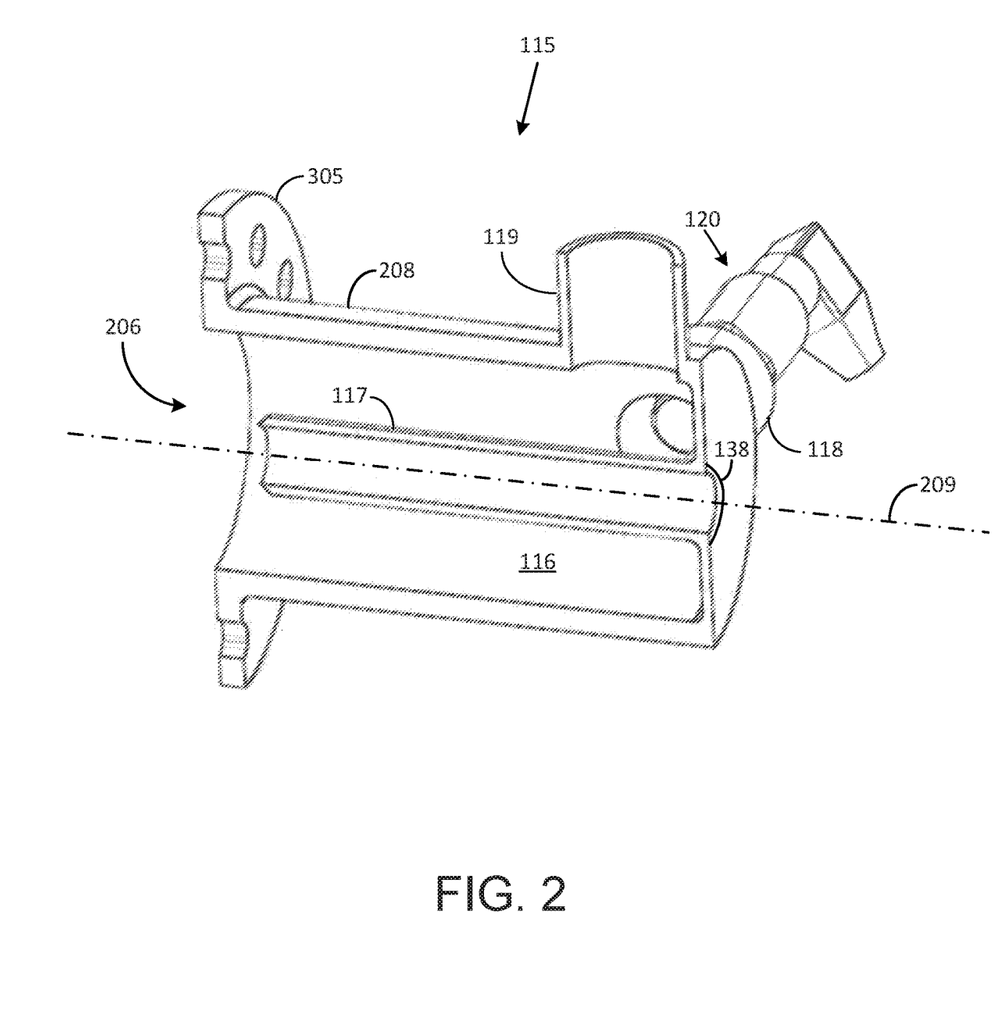
FIG. 2 shows an exemplary implementation of a bi-directional oil-flow adapter in accordance with an embodiment of the disclosure.

FIG. 2 shows an exemplary implementation of the bi-directional oil-flow adapter 115 in accordance with an embodiment of the disclosure. In this exemplary implementation, the bi-directional oil-flow adapter 115 can include a flange 305 that can be used to mechanically couple the bi-directional oil-flow adapter 115 to the valve-controlled port 110 (shown in FIG. 1). The flange 305 can be located at one end of a cylindrical body portion 208 that includes an opening 206 through which oil enters the bi-directional oil-flow adapter 115 from the valve-controlled port 110. The oil outlet port 119 can be located at an opposing end of the cylindrical body portion 208. Also located at the opposing end of the cylindrical body portion 208 can be an oil inlet port 128 that is coupled to the pump 128 (via a control valve 134 as shown in FIG. 1).

The cylindrical internal surface of the cylindrical body portion 208 can constitute a peripheral circumference of the first conduit 116. Arranged concentric to the cylindrically-shaped internal surface of the cylindrically-shaped body portion 208 (i.e., the first conduit 116) can be a cylindrically-shaped pipe that constitutes the second conduit 117. It can be understood that each of a longitudinal axis of the first conduit 116 and a longitudinal axis of the second conduit 117 can coincide with a longitudinal axis 209 of the bi-directional oil-flow adapter 115.

The pressure sensor 120 can be coupled into the bi-directional oil-flow adapter 115 at one of various openings provided in the cylindrical body portion 208, such as the pressure monitoring port 118 located near the oil outlet port 119.

Figure 3:
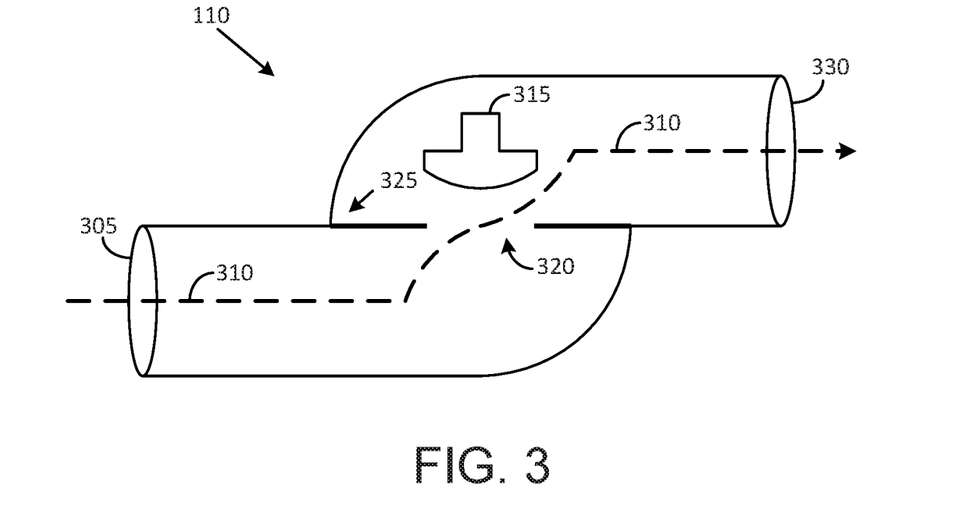
FIG. 3 illustrates a first oil flow characteristic when oil is drawn through the valve-controlled port by using the bi-directional oil-flow adapter in accordance with an embodiment of the disclosure.

FIG. 3 illustrates an example first oil flow characteristic 310 when oil is drawn through an opening 305 in the valve-controlled port 110, when the valve-controlled port 110 is coupled to the transformer housing 106, according to an embodiment of the disclosure. In this exemplary implementation, the valve-controlled port 110 can include a gate valve 315 that blocks the flow of oil when actuated to block the internal opening 320. On the other hand, when the gate valve 315 is actuated to unblock the internal opening 320, oil can flow through the valve-controlled port 110 along the first oil flow characteristic 310 (indicated by the dashed line) and out through the opening 330 (into the bi-directional oil-flow adapter 115). As can be understood from the first oil flow characteristic 310, an area 325 of the valve-controlled port 110 can accumulate stagnant oil as a result of being located away from the main oil flow path (designated by the first oil flow characteristic 310). It can be undesirable that the oil remains stagnant in nooks and crannies, such as the area 325, for various reasons. One of these reasons can be attributed to the stagnant oil constituting a stale oil sample that does not replicate the characteristics of the oil contained inside the transformer housing 106 and can provide misleading results if drawn through the valve-controlled port 110 and into the bi-directional oil-flow adapter 115 for sampling purposes.

Figure 4:
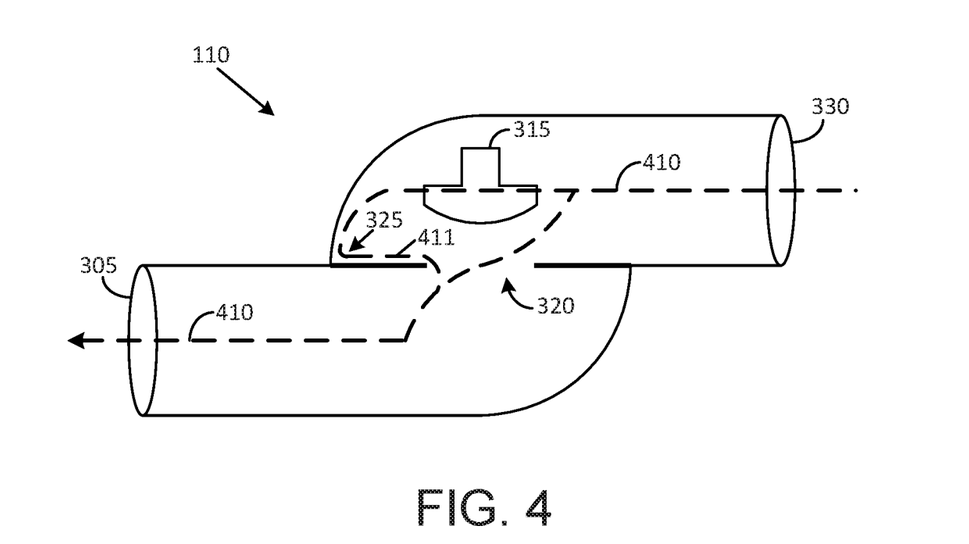
FIG. 4 illustrates a second oil flow characteristic when oil is injected into the valve-controlled port by using the bi-directional oil-flow adapter in accordance with an embodiment of the disclosure.

FIG. 4 illustrates an example second oil flow characteristic 410 when the sampled oil is forcefully injected into the valve-controlled port 110 via the opening 330 from the bi-directional oil-flow adapter 115, according to an embodiment of the disclosure. The forceful injection of the sample oil (by using the pump 128 shown in FIG. 1) can flush out any stagnant oil that may be present in locations such as the area 325 thereby ensuring that the next oil sample drawn from the transformer housing 106 via the valve-controlled port 110 more accurately represents the oil contained inside the transformer housing 106. In addition to flushing the valve-controlled port 110, the forceful injection of the sample oil can also flush out stale oil from other locations such as in the bi-directional oil-flow adapter 115, and/or in pipework associated with the bi-directional oil-flow adapter 115 and/or the valve-controlled port 110.

Figure 5:
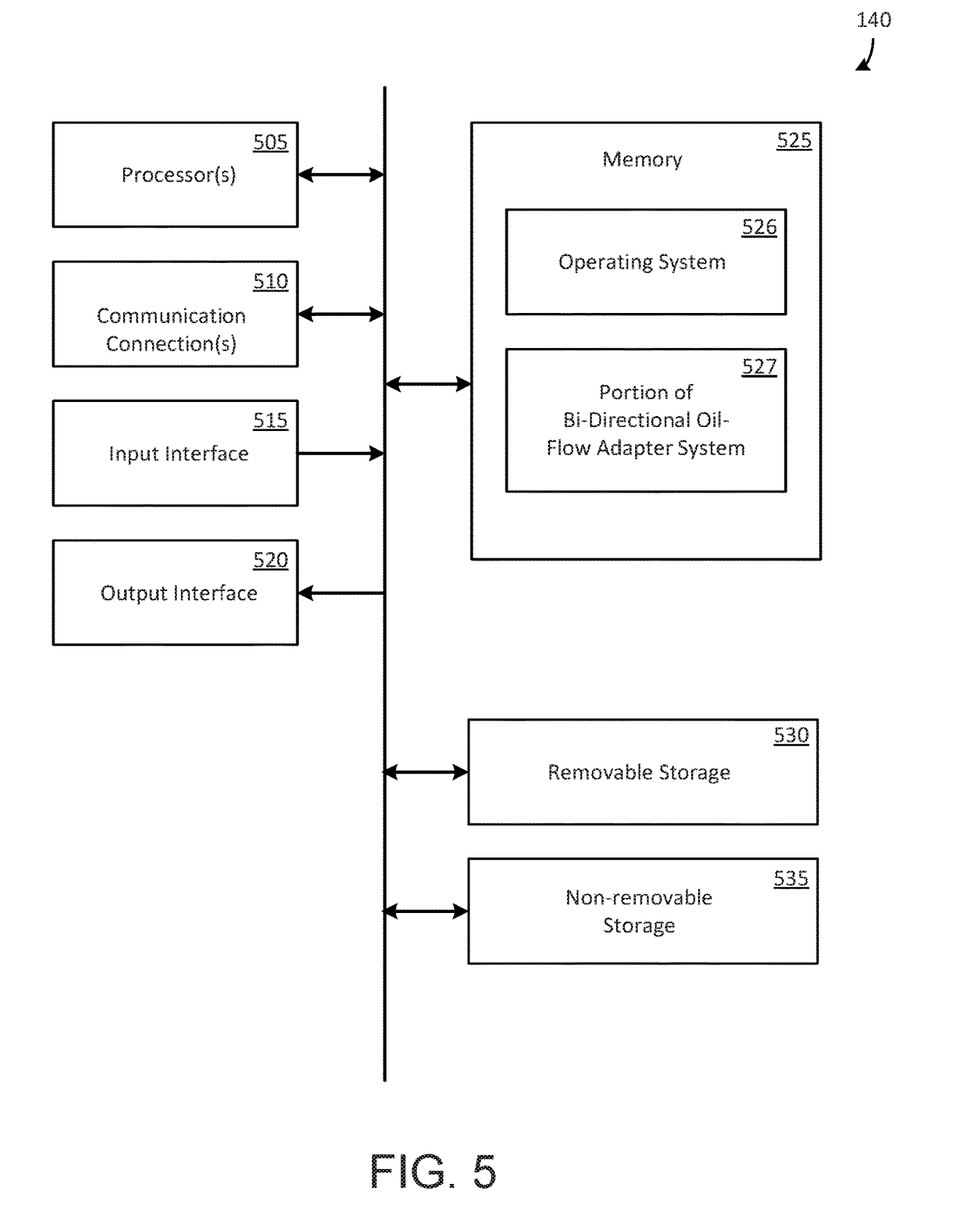
FIG. 5 illustrates an example computer incorporating a processor for executing an oil sampling procedure upon a transformer by using a bi-directional oil-flow adapter in accordance with an embodiment of the disclosure.

FIG. 5 illustrates an example computer 140 incorporating one or more processors, such as a processor 505, for executing an oil sampling procedure upon the transformer 105 by using a bi-directional oil-flow adapter 115 in accordance with an embodiment of the disclosure. The processor 505 can be configured to communicatively cooperate with various elements contained in the system 100 shown in FIG. 1, including a memory 525. The processor 505 can be implemented and operated using appropriate hardware, software, firmware, or combinations thereof. Software or firmware implementations can include computer-executable or machine-executable instructions written in any suitable programming language to perform the various functions described. In one embodiment, instructions associated with a function block language can be stored in the memory 525 and executed by the processor 505.

The memory 525 can be used to store program instructions that are loadable and executable by the processor 505, as well as to store data generated during the execution of these programs. Depending on the configuration and type of the system 100, the memory 525 can be volatile (such as random access memory (RAM)) and/or non-volatile (such as read-only memory (ROM), flash memory, etc.). In some embodiments, the memory devices can also include additional removable storage 530 and/or non-removable storage 535 including, but not limited to, magnetic storage, optical disks, and/or tape storage. The disk drives and their associated computer-readable media can provide non-volatile storage of computer-readable instructions, data structures, program modules, and other data. In some implementations, the memory 525 can include multiple different types of memory, such as static random access memory (SRAM), dynamic random access memory (DRAM), or ROM.

The memory 525, the removable storage, and the non-removable storage are all examples of non-transient computer-readable storage media. Such non-transient computer-readable storage media can be implemented in any method or technology for storage of information such as computer-readable instructions, data structures, program modules or other data. Additional types of non-transient computer storage media that can be present include, but are not limited to, programmable random access memory (PRAM), SRAM, DRAM, ROM, electrically erasable programmable read-only memory (EEPROM), compact disc read-only memory (CD-ROM), digital versatile discs (DVD) or other optical storage, magnetic cassettes, magnetic tapes, magnetic disk storage or other magnetic storage devices, or any other medium which can be used to store the desired information and which can be accessed by the processor 505. Combinations of any of the above should also be included within the scope of non-transient computer-readable media.

Turning to the contents of the memory 525, the memory 525 can include, but is not limited to, an operating system (OS) and one or more application programs or services for implementing the features and aspects disclosed herein. Such applications or services can include software and/or firmware portions of the system 100 that is associated with the bi-directional oil-flow adapter 527, such as for processing one or more signals provided by the DGA 135, actuating various automatically controlled valves (such as the valve 127, for example), and processing various alarm/warning/status signals provided by the malfunction detection system 130.

Figure 6:
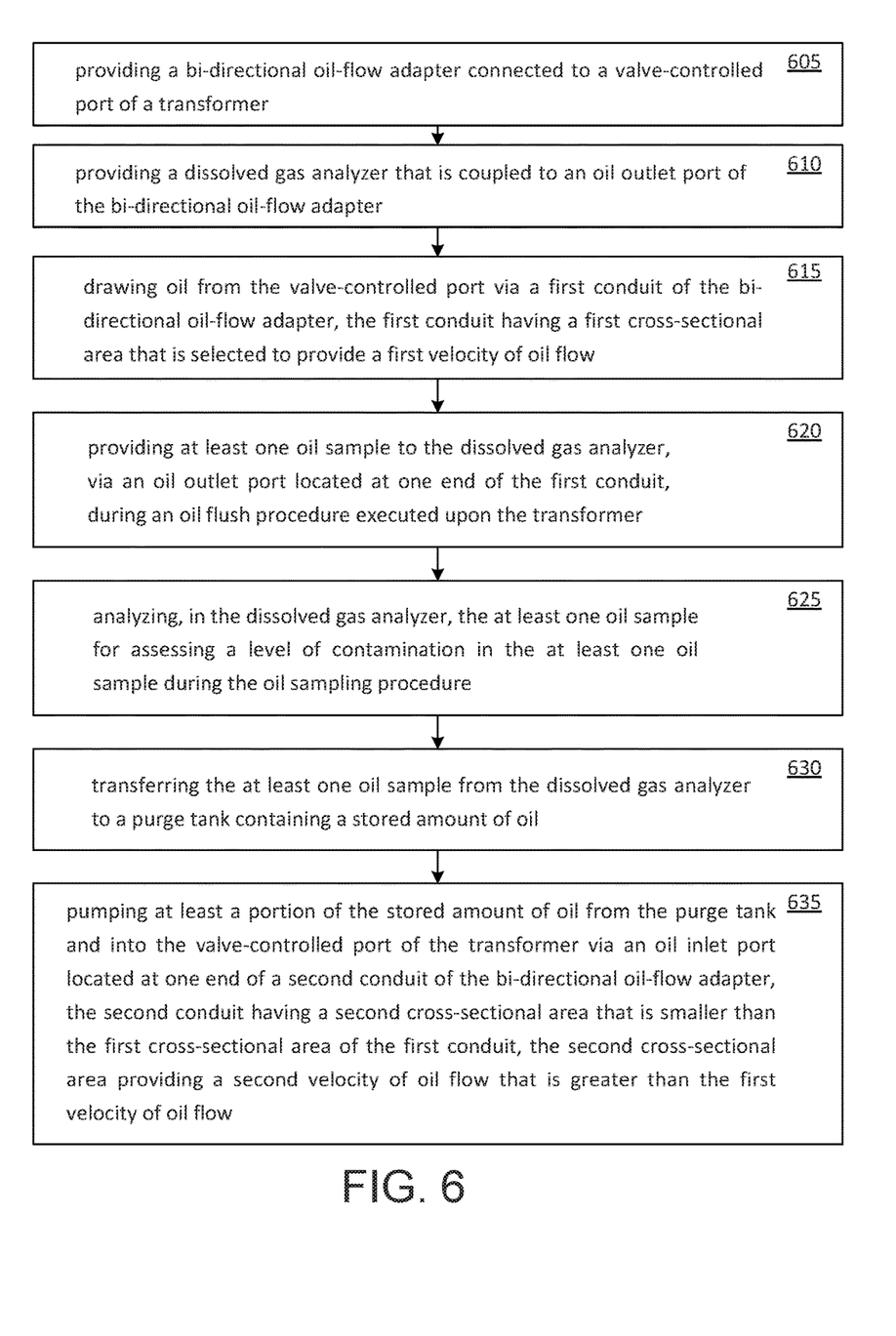
FIG. 6 illustrates an example flowchart of a method for executing an oil sampling procedure upon a transformer by using a bi-directional oil-flow adapter in accordance with an embodiment of the disclosure.

FIG. 6 illustrates an example flowchart of a method for executing an oil sampling procedure upon a transformer by using a bi-directional oil-flow adapter 115 in accordance with an embodiment of the disclosure. The various blocks of the example flowchart are described here with reference to FIG. 1. Block 605 pertains to providing a bi-directional oil-flow adapter 115 connected to a valve-controlled port 110 of a transformer. Block 610 pertains to providing a dissolved gas analyzer 135 that is coupled to an oil outlet port 119 of the bi-directional oil-flow adapter 115. A gas sensor assembly 125 can be optionally included to provide to the DGA 135, one or more signals indicative of a rate of release of at least one gas contained in an oil sample. Block 615 pertains to drawing oil from the valve-controlled port 110 via a first conduit 116 of the bi-directional oil-flow adapter 115, the first conduit 116 having a first cross-sectional area that is selected to provide a first oil flow velocity. Block 620 pertains to providing at least one oil sample to the DGA 135, via the oil outlet port 119 that is located at one end of the first conduit 116. Block 625 pertains to analyzing, in the DGA 135, the at least one oil sample for evaluating at least one gas content in the at least one oil sample. A number of oil samples can be analyzed by the DGA 135 over a period of time. Block 630 pertains to transferring the at least one oil sample from the DGA 135 to a purge tank 145 containing a volume of oil. Block 635 pertains to pumping at least a portion of the volume of oil from the purge tank 145 and into the valve-controlled port 110 of the transformer 105 via an oil inlet port 138 located at one end of a second conduit 117 of the bi-directional oil-flow adapter 115, the second conduit 117 having a second cross-sectional area that is smaller than the first cross-sectional area of the first conduit 116, the second cross-sectional area providing a second oil flow velocity that is greater than the first oil flow velocity.

Many modifications and other embodiments of the example descriptions set forth herein to which these descriptions pertain will come to mind having the benefit of the teachings presented in the foregoing descriptions and the associated drawings. Thus, it will be appreciated the disclosure may be embodied in many forms and should not be limited to the exemplary embodiments described above. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That claimed disclosure is:

1. A system comprising:
  a transformer comprising a valve-controlled port for use when accessing oil contained inside the transformer;
  a bi-directional oil-flow adapter that is attachable to the valve-controlled port, the bi-directional oil-flow adapter comprising:
  an oil outlet port configured to output an oil sample acquired from the transformer via the valve-controlled port and the bi-directional oil-flow adapter when the bi-directional oil-flow adapter is attached to the valve-controlled port;
  a first conduit contained inside the bi-directional oil-flow adapter, the first conduit having a first cross-sectional area that is selected to provide a first oil flow velocity to the oil sample when flowing from the valve-controlled port and through the bi-directional oil-flow adapter to the oil outlet port;

an oil inlet port configured to accept an inflow of a volume of oil into the bi-directional oil-flow adapter; and a second conduit contained inside the bi-directional oil-flow adapter, the second conduit having a second cross-sectional area that is smaller than the first cross-sectional area, the second cross-sectional area selected to provide a second oil flow velocity to the volume of oil when flowing from the oil inlet port and through the bi-directional oil-flow adapter into the valve-controlled port, the second oil flow velocity higher than the first oil flow velocity; and a dissolved gas analyzer coupled to the oil outlet port of the bi-directional oil-flow adapter, the dissolved gas analyzer operable to analyze the oil sample for evaluating at least one gas content of the oil sample;

a purge tank configured to store the volume of oil, wherein the purge tank is further configured to store an oil sample as a part of the volume of oil, after analyzing by the dissolved gas analyzer; and a pump that is operable to pump the volume of oil from the purge tank and into the oil inlet port of the bi-directional oil-flow adapter.

2. The system of claim 1, further comprising:
a pressure sensor attached to the bi-directional oil-flow adapter; and
a malfunction detection system coupled to at least one of the pressure sensor or the dissolved gas analyzer, the malfunction detection system configured to obtain at least one of an oil pressure reading from the pressure sensor or a gas level indication from the dissolved gas analyzer and to use the at least one of the oil pressure reading or the gas level indication to determine a malfunctioning of the valve-controlled port.

3. The system of claim 1, further comprising:
a gas sensor assembly coupled to the oil outlet port of the bi-directional oil-flow adapter, the gas sensor assembly configured to detect a rate of release of at least one gas contained in the oil sample and to generate one or more sensor signals that are provided to the dissolved gas analyzer.

4. The system of claim 3, wherein the at least one gas is a low-k gas selected from a family of gases, the family of gases comprising hydrogen and carbon monoxide.

5. A bi-directional oil-flow adapter that is attachable to a valve-controlled port of a transformer, the bi-directional oil-flow adapter comprising:
an oil outlet port outputting an oil sample acquired from the transformer via the valve-controlled port and the bi-directional oil-flow adapter when the bi-directional oil-flow adapter is attached to the valve-controlled port;
a first conduit contained inside the bi-directional oil-flow adapter, the first conduit having a first cylindrically-shaped cross-sectional area that is selected to provide a first oil flow velocity to the oil sample when flowing from the valve-controlled port and through the bi-directional oil-flow adapter to the oil outlet port;
an oil inlet port accepting an inflow of a volume of oil, the volume of oil including the sample of oil and an additional amount of oil, into the bi-directional oil-flow adapter; and
a second conduit contained inside the bi-directional oil-flow adapter, the second conduit concentrically inside the first conduit, the second conduit being fixed in length and not projecting through the bi-directional flow adapter at the valve-controlled port attachment, the second conduit having a second cylindrically-shaped cross-sectional area that is smaller than the first cylindrically-shaped cross-sectional area, the second cylindrically-shaped cross-sectional area selected to provide a second oil flow velocity to the volume of oil when flowing from the oil inlet port and through the bi-directional oil-flow adapter into the valve-controlled port, the second oil flow velocity higher than the first oil flow velocity, wherein the second oil flow velocity of the volume of oil purges the valve-controlled port of old or stagnant oil.

6. The bi-directional oil-flow adapter of claim 5, wherein each of a longitudinal axis of the first conduit and a longitudinal axis of the second conduit coincides with a longitudinal axis of the bi-directional oil-flow adapter.

7. The bi-directional oil-flow adapter of claim 5, wherein the first conduit is arranged concentric to the second conduit.

8. The bi-directional oil-flow adapter of claim 5, further comprising a pressure sensor operable to obtain an oil pressure reading of oil contained in the bi-directional oil-flow adapter.

9. A method comprising:
providing a bi-directional oil-flow adapter connected to a valve-controlled port of a transformer;
providing a dissolved gas analyzer that is coupled to an oil outlet port of the bi-directional oil-flow adapter;
drawing oil from the valve-controlled port via a first conduit of the bi-directional oil-flow adapter, the first conduit having a first cross-sectional area that is selected to provide a first oil flow velocity;
providing at least one oil sample to the dissolved gas analyzer, via the oil outlet port that is located at one end of the first conduit;
analyzing, in the dissolved gas analyzer, the at least one oil sample for evaluating at least one gas content in the at least one oil sample;
transferring the at least one oil sample from the dissolved gas analyzer to a purge tank containing a volume of oil; and
pumping at least a portion of the volume of oil from the purge tank and into the valve-controlled port of the transformer via an oil inlet port located at one end of a second conduit of the bi-directional oil-flow adapter, the second conduit having a second cross-sectional area that is smaller than the first cross-sectional area of the first conduit, the second cross-sectional area providing a second oil flow velocity that is greater than the first oil flow velocity.

10. The method of claim 9, wherein the at least one gas content in the at least one oil sample is indicative of a contaminant in oil contained inside the transformer.

11. The method of claim 10, wherein the second oil flow velocity is directed at purging oil from an area inside at least one of the bi-directional oil-flow adapter, the valve-controlled port, or pipework associated with at least one of the bi-directional oil-flow adapter or the valve-controlled port.

12. The method of claim 10, wherein the at least one oil sample comprises a plurality of oil samples obtained by the dissolved gas analyzer from the transformer over a period of time.

13. The method of claim 12, further comprising:
coupling a pressure sensor to a pressure sensing port of the bi-directional oil-flow adapter;
using the pressure sensor to obtain an oil pressure reading of oil contained in the bi-directional oil-flow adapter; and determining from the oil pressure reading, a malfunctioning of the valve-controlled port.

14. The method of claim 13, wherein the malfunctioning of the valve-controlled port is characterized by at least one of the oil pressure reading exceeding a first threshold pressure or the oil pressure reading falling below a second threshold pressure.

15. The method of claim 9, further comprising:
detecting a rate of release of at least one gas contained in the at least one oil sample and generating one or more sensor signals that are coupled into the dissolved gas analyzer.

16. The method of claim 15, wherein the at least one gas is a low-k gas selected from a family of gases, the family of gases comprising hydrogen and carbon monoxide.

17. The method of claim 15, further comprising:
detecting a malfunctioning of the valve-controlled port based at least in part on the rate of release of the at least one gas contained in the at least one oil sample.

18. The method of claim 17, further comprising:
transmitting one of a warning or an alarm to a computer that is communicatively coupled to the dissolved gas analyzer.

* * * * *